US 6,232,295 B1

(12) United States Patent
Kayyem et al.

(10) Patent No.: US 6,232,295 B1
(45) Date of Patent: *May 15, 2001

(54) CELL-SPECIFIC CONTRAST AGENT AND GENE DELIVERY VEHICLES

(76) Inventors: Jon Faiz Kayyem, 428 S. Sierra Bonita, Pasadena, CA (US) 91106; Thomas J. Meade, 1656 New York Dr., Altadena, CA (US) 91001; Scott E. Fraser, 720 Bison Ave., Newport Beach, CA (US) 92660

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/321,552

(22) Filed: Oct. 12, 1994

(51) Int. Cl.$^7$ ............................ A61K 48/00; A61K 49/14; A61K 49/18
(52) U.S. Cl. ............................ 514/44; 435/455; 424/9.1; 424/9.2; 424/9.3; 424/9.32; 424/9.34; 424/9.36; 424/9.364; 424/9.365
(58) Field of Search .................................. 424/9, 9.1, 9.2, 424/9.3, 9.32, 9.34, 9.36, 9.364, 9.365; 514/44, 2; 435/172.3, 69.1, 455

(56) References Cited

U.S. PATENT DOCUMENTS

| | | | |
|---|---|---|---|
| 4,104,466 | 8/1978 | Tsuchida et al. | 542/433 |
| 4,284,537 | 8/1981 | Beachey | 260/6 |
| 4,701,521 | 10/1987 | Ryser et al. | 530/300 |
| 4,847,240 | 7/1989 | Ryser et al. | 530/300 |
| 5,059,415 | 10/1991 | Neuwelt | 424/9 |
| 5,155,215 | 10/1992 | Ranney | 424/9.1 |
| 5,230,883 * | 7/1993 | Kornguth et al. | 424/9 |
| 5,241,060 | 8/1993 | Engelhardt et al. | 536/27.1 |
| 5,274,119 | 12/1993 | Frazier et al. | 548/521 |

FOREIGN PATENT DOCUMENTS

| | | |
|---|---|---|
| 0253202 | 1/1988 | (EP) . |
| 0388758 | 9/1990 | (EP) . |
| WO93 01837 | 2/1993 | (WO) . |

OTHER PUBLICATIONS

Diwu, Zhenjun and J. William Lown, "Phototherapeutic Potential of Alternative Photosensitizers to Porphyrins." *Pharmac. Ther.*, 63:1–35 (1994).
Heindel, N.D., et al., "Macromolecular Attachment as a Metabolic Stabilizer for a Labile Radiosensitizer," *J. Pharm. Sci.*, 76(5):384–386 (1987).
Hamblin, M.R., et al., "Photosensitizer Targeting in Photodynamic Therapy: I. Conjugates of Haematoporphyrin with Albumin and Transferrin," *Journal of Photochemistry and Photobiology*, 26:45–56 (1994).
Flynn, G., et al., "Magnetically Responsive Photosensitizing Reagents for Possible Use in Photoradiation Therapy," *Cancer Letters*, 78:109–114 (1994).

Pandey et al., "Photochemical Linking of Primary Aromatic Amines to Carrier Proteins to Elicit Antibody Response Against the Amine Haptens," *J. Of Immunological Methods*, 94:237–246 (1986).
Cotten et al., "Transferrin–Polycation–Mediated Introduction of DNA into Human Leukemic Cells: Stimulation by Agents that Affect the Survival of Transfected DNA or Modulate Transferrin Receptor Levels." *PNAS USA*, 87:4033–4037 (1990).
Oser et al., "Sensitive Non–Radioactive Dot–Blot Hybridization Using DNA Probes Labelled with Chelate Group Substituted Psoralen and Quantitative Detection by Europium Ion Fluorescense," *Nucleic Acid Res.*, 16(3):1181–1196 (1988).
Curiel et al., "Gene Transfer to Respiratory Epithelial Cells via the Receptor–Mediated Endocytosis Pathway," *Am. J. Respir. Cell. Mol. Biol.*, 6(3):247–252 (1992).
Curiel et al., "Adenovirus Enhancement of Transferrin–Polylysine–Mediated Gene Delivery," *Proc. Natl. Acad. Sci. USA*, 88:8850–8854 (1991).
Kumar, K., et al., "Ligand Basicity and Rigidity Control Formation of Macrocyclic Polyamino Carboxylate Complexes of Gadolinium (III)", *Inorg. Chem.*, 32:4193–4199, (1993).
Lex, L., "Development of Contrast Enhancing Agents in Magnetic Resonance Imaging", *Acta Biochim. Biophys. Hung.*,24/3:265–281, (1989).
Grossweiner, L.I., "Photodynamic Therapy with Porphyrin Derivatives", *American Porphyric Pesticides* Ch. 18:255–265, (1994).
Paajanen, H., et al., "Proton Relaxation Enhancement of Albumin, Immunoglobulin G, and Fibrinogen Labeled with Gd–DTPA", *Magnetic Resonance in Medicine*, 13:38–43, (1990).
Behr, Jean–Paul, "Gene Transfer with Synthetic Cationic Amphiphiles: Prospects for Gene Therapy", *Bioconjugate Chem.*, 5:382–389, (1994).

(List continued on next page.)

*Primary Examiner*—Scott D. Priebe
(74) *Attorney, Agent, or Firm*—Richard F. Trecartin; Flehr Hohbach Test Albritton & Herbert LLP; Robin M. Silva

(57) ABSTRACT

A delivery vehicle is described that is capable of being specifically bound to and taken into targeted cells, delivering numerous paramagnetic ions for magnetic resonance imaging (MRI) of the cells. The delivery vehicle comprises a polymeric molecule having a net positive charge complexed with another polymeric molecule having a net negative charge. Cell targeting moieties and MRI contrast agents are attached to one or both of the polymeric molecules. In one embodiment, the polymeric molecule having a net negative charge is a nucleic acid. Thus, the delivery vehicles can be used in clinical protocols in which nucleic acids for gene therapy and agents for MRI contrast are co-transported to specific cells allowing medical imaging monitoring of nucleic acid delivery.

2 Claims, 3 Drawing Sheets

OTHER PUBLICATIONS

Schwendener, R.A., "Liposomes and Immunoliposomes as Carriers for Cytostatic Drugs, Magnetic Resonance Contrast Agents, and Fluorescent Chelates", *Chimia*, 46:69–77, (1992).

Zatloukal, K., et al., "Somatic gene therapy for cancer: the utility of transferrinfection in generating 'tumor vaccines'", *Gene*, 135:199–207, (1993).

DeMagalhaes–Silverman, M., et al., "Bone Marrow Transplantation on a Review", *Cell Transplantation*, 2:75–98, (1993).

Gutierrez, A.A., et al., "Gene therapy for cancer", *The Lancet*, 339:715–721, (1992).

Renn, Oliver, et al., "Large–Scale Synthesis of the Bifunctional Chelating Agent (2–(p–Nitrobenzyl)–1,4,7,10–tetraazacyclododecane–N,N',N'',N'''–tetraacetic Acid, and the Determination of Its Enantiomeric Purity by Chiral Chromatography", *Bioconjugate Chem.*, 3:563–569, (1992).

McMurry, T.J., et al., "Convenient Synthesis of Bifunctional Tetraaza Macrocycles", *Bioconjugate Chem.*, 3:108–117, (1992).

Moi, M.K., et al., "The Peptide Way to Macrocyclic Bifunctional Chelating Agents: Synthesis of 2–(p–Nitrobenzyl)–1,4,7,10–tetraazacyclododecane–N,N',N'',N'''–tetraacetic Acid and Study of Its Yttrium(III) Complex", *J. Am. Chem. Soc.*, 110:6266–6267, (1988).

Tweedle, M.F., et al., "Considerations Involving Paramagnetic Coordination Compounds as Useful NMR Contrast Agents", *Nucl. Med. Biol.*, 15(1): 31–36, (1988).

Cotton, Matt, et al., "High–efficiency receptor–mediated delivery of small and large (48 kilobase gene constructs using the endosome–disruption activity of defective or chemically inactivated adenovirus particles", *Proc. Natl. Acad. Sci, U.S.A.*, 89:6094–6098, (1992).

Cotton, Matt, et al., "Receptor–Mediated Transport of DNA into Eukaryotic Cells", *Methods in Enzymology*, 217:618–645, (1993).

Hnatowich, D.J., et al., "The Preparation of DTPA–Coupled Antibodies Radiolabeled with Metallic Radionuclides: an Improved Method", *Journal of Immunological Methods*, 65:147–157, (1983).

Kabanov, A. V., et al., "DNA Interpolyelectrolyte Complexes as a Tool for Efficient Cell Transformation", *Biopolymers*, 31:1437–1443, (1991).

Kahn, M.L, et al., "Optimization of Retroviral Vector–Mediated Gene Transfer into Endothelial Cells in Vivo", *Circulation Resesarch*, 71(6):1508–1517, (1992).

Shen, T., et al., "Monocrystalline Iron Oxide Nanocompounds (MION): Physicochemical Properties", *MRM*, 29:599–604, (1993).

Slinkin, M.A., et al., "Terminal–Modified Polylysine–Based Chelating Polymers: Highly Efficient Coupling to Antibody with Minimal Loss in Immunoreactivity", *Bioconjugate Chem.*, 2:342–438, (1991).

Torchilin, V. P., et al., "Monoclonal Antibody Modification with Chelate–Linked High–Molecular–Weight Polymers: Major Increases in Polyvalent Cation Binding without loss of Antigen Binding", *Hybridoma*, 6(3):229–240, (1987).

Torchilin, V.P., et al., "The Antibody–Linked Chelating Polymers for Nuclear Therapy and Diagnostics", *Critical Reviews in Therapeutic Drug Carrier System*, 7(4):275–308, (1991).

Trubetskoy, V.S., et al., "Cationic liposomes enhance targeted delivery and expression of exogenous DNA mediated by N–terminal modified poly(L–lysine)–antibody conjugate in mouse lung endothelial cells", *Biochimica et Biophysica Acta*, 1131:311–313, (1992).

Trubetskoy, V.S., et al., "Use of N–Terminal Modified Poly(L–lysine)–Antibody Conjugate as a Carrier for Targeted Gene Delivery in Mouse Lung Endothelial Cells", *Bioconjugate Chem.*, 3:323–327, (1992).

Unger, E.C., et al., "Magnetic Resonance Imaging Using Gadolinium Labeled Monoclonal Antibody", *Investigative Radiology*, 693–700, (Oct.,1985).

Wagner, E., et al., "Transferrin–polycation conjugates as carriers for DNA uptake into cells", *Proc. Natl. Acad. Sci. USA*, 87:3410–3414, (1990).

Wagner, E., et al., "Transferrin–polycation–DNA complexes: The effect of polycations on the structure of the complex and DNA delivery to cells", *Proc. Natl. Acad. Sci. USA*, 88:4255–4259, (1991).

Wagner, E., et al., "Coupling of adenovirus to transferring–polylysine/DNA complexes greatly enhances receptor–mediated gene delivery and expression of transfected genes", *Proc. Natl. Acad. Sci. USA*, 89:6099–6103, (1992).

Wagner, E., et al., "DNA–Binding Transferrin Conjugates as Functional Gene–Delivery Agents: Synthesis by Linkage of Polylysine or Ethidium Homodimer to the Transferrin Carbohydrate Moiety", *Bioconjugate Chem.*, 2:226–231, (1991).

Wagner, E., et al., "Influenza virus hemagglutinin HA–2–terminal fusogenic peptides augment gene transfer by transferrin–polylysine–DNA complexes: Toward a synthetic virus–like gene–transfer vehicle", *Proc. Natl. Acad. Sci. USA*, 89:7934–7938, (1992).

Weissleder, R., et al., "Drug Targeting in Magnetic Resonance Imaging", *Magnetic Resonance Quarterly*, 8(1):55–63, (1992).

Wu, G.Y., et al., "Receptor–mediated Gene Delivery in vivo", *The Journal of Biological Chemistry*, 266(22):14338–14342, (1991).

Zenke, M., et al., "Receptor–mediated endocytosis of transferrin–polycation conjugates: An efficient way to introduce DNA into hematopoietic cells", *Proc. Natl. Acad. Sci. USA*, 87:3655–3659, (1990).

Wu, George Y., "Receptor–mediated Gene Delivery in Vivo", The Journal of Biological Chemistry vol. 266, No. 22 Issue of Aug. 5, pp. 14338–14342, 1991.*

* cited by examiner

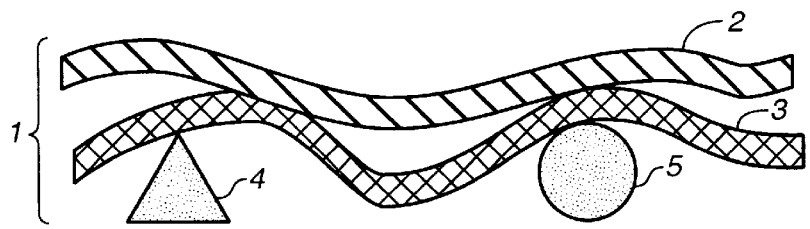
FIG._1A
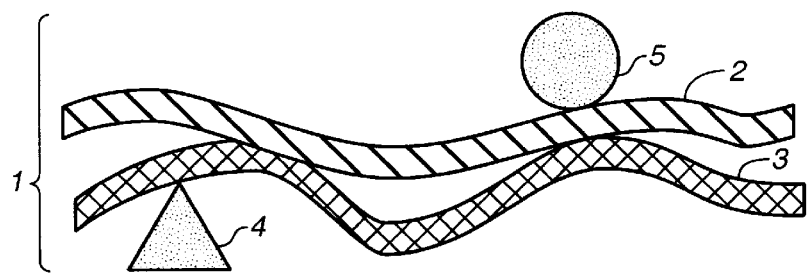
FIG._1B
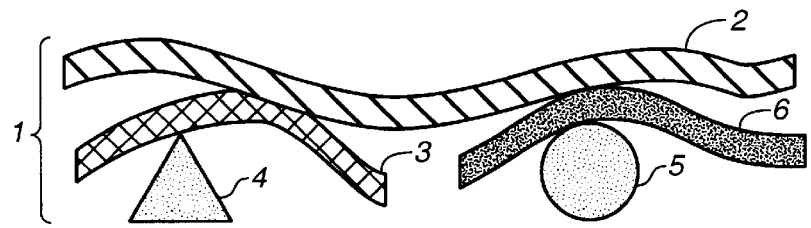
FIG._1C
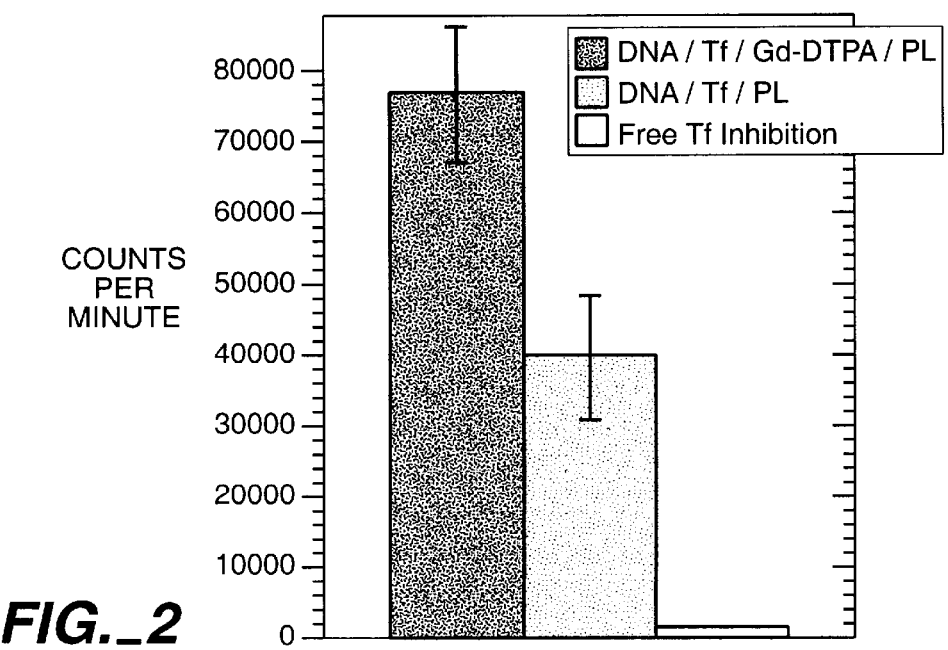
FIG._2

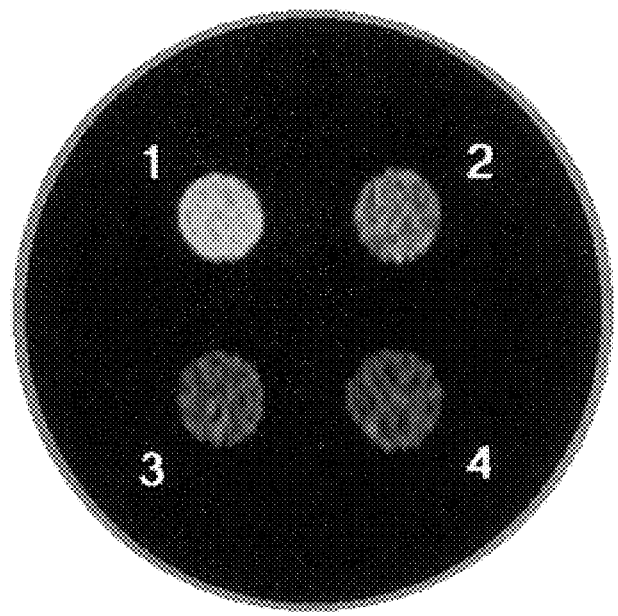
FIG._3

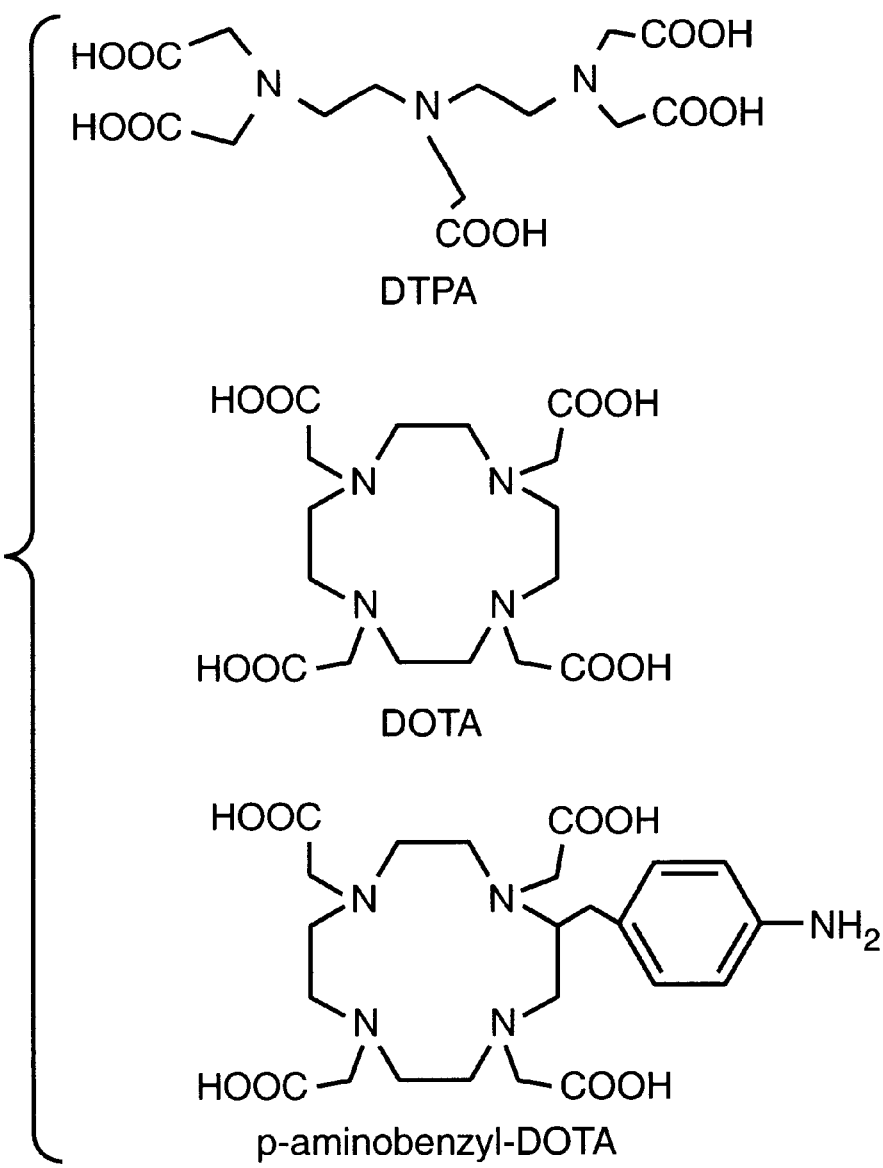
FIG._4

CELL-SPECIFIC CONTRAST AGENT AND GENE DELIVERY VEHICLES

BACKGROUND OF THE INVENTION

In recent years, magnetic resonance imaging (MRI) has emerged as a powerful tool in clinical settings because it is noninvasive and yields an accurate volume rendering of the subject. The image is created by imposing one or more orthogonal magnetic field gradients upon the specimen while exciting nuclear spins with radio frequency pulses as in a typical nuclear magnetic resonance (NMR) experiment. After collection of data with a variety of gradient fields, deconvolution yields a one, two, or three dimensional image of the specimen. Typically, the image is based upon the NMR signal from the protons of water where the signal intensity in a given volume element is a function of the water concentration and relaxation times ($T_1$ and $T_2$). Local variations in these three parameters provide the vivid contrast observed in MR images. For example, the low water content of bone makes it distinctively dark, while the short $T_2$ of clotted blood affords it a higher signal intensity than that from non-clotted blood.

The same advantages that have made MRI the technique of choice in medical imaging make it an ideal imaging tool for use in biological experiments. Unlike light-microscope imaging techniques based upon the use of dyes or fluorochromes, MRI does not produce toxic photobleaching by-products. Furthermore, unlike light-microscopy, MRI is not limited by light scattering or other optical aberrations to cells within approximately only one hundred microns of the surface. MRI was originally considered a purely noninvasive approach but more recently it has been found that contrast agents can significantly improve the diagnostic utility of the technique. MRI contrast agents dramatically reduce the relaxation times of protons in the surrounding water. The ion $Gd^{3+}$, in its non-toxic chelated forms, is the most commonly used paramagnetic ion because of its large magnetic dipole and large effect on relaxation times. For example, $Gd^{3+}$ chelated with diethylenetriaminepentaacetic acid (DTPA) is a vascular contrast agent now widely used in diagnostic radiology. The chemical structure of DTPA is depicted in FIG. 4.

Traditional MRI offers high spatial resolution and multiple plane imaging in a fast noninvasive procedure. When MRI contrast agents are used diagnostically, they are vascularly perfused, enhancing the contrast of blood vessels and reporting on organ lesions and infiltration. However, the labeling of specific tissues for diagnostic radiology remains a difficult challenge for MRI. Efforts to develop cell and tissue-specific MRI contrast agents by modifying existing immunological techniques has been the focus of much research in diagnostic radiology. For example, antibodies labeled with paramagnetic ions, generally the gadolinium chelate Gd-DTPA, have been generated and tested for their effects on MRI contrast of tumors and other tissues [Lex, Acta Biochim. Biophys. Hung. 24:265–281 (1989); U.S. Pat. No. 5,059,415]. It was anticipated that due to reductions in the rate of molecular tumbling, Gd-DTPA when bound to antibodies would show significantly higher relaxivity, a measure of MRI contrast enhancement, than that of unbound Gd-DTPA. This increase in relaxivity per Gd ion, it was hoped, would generate sufficient signal for tissue contrast to be observed using antibodies labeled with 10–50 Gd ions per protein molecule.

Unfortunately, the relaxivity of Gd bound to antibodies has been found to be only slightly better than that of unbound Gd-DTPA [Paajanen et al., Magn. Reson. Med 13:38–43 (1990)]. Therefore, to generate detectable contrast enhancement in an antibody-labeled tissue, the immunological reagent must be conjugated with hundreds if not thousands of Gd ions per antibody. Currently this is unattainable using standard techniques.

Several researchers have examined the possibility that the number of Gd ions per antibody could be increased by conjugating polylysine to the antibody, then labeling the polylysine extensively with Gd-DTPA [WO93/01837]. So far, these attempts have shown only limited success in part due to the unfavorable ionic and steric effects of conjugating antibodies to large polymers.

Research in the field of targeted MRI contrast agents has thus turned to the use of iron oxide particles as high signal strength $T_2$ contrast agents [Shen et al., Magnet. Res. Med. 29:599–604 (1993); Weissleder et al., Magnetic Resonance Quarterly, 8:55–63 (1992)]. However, no iron oxide particles have yet been approved for use in humans.

Liposomes as carriers of contrast media show promise as tissue-specific MRI agents as well [Schwendener, R. A., Chimia 46:69–77 (1992)]. Two classes of such contrast agents have been developed: (i) water soluble contrast agents entrapped between phospholipid bilayers, and (ii) liposomes directly incorporating amphipatic molecules covalently attached to MRI contrast agents such as Gd-DTPA. The former class of liposomal contrast agents suffers from leakiness of the water soluble agent in vivo, and the later from long-term retention of the agent in the liver and spleen. Nevertheless, liposomes show promise as liver, spleen and lung contrast agents.

SUMMARY OF THE INVENTION

Based on the foregoing it is apparent that there exists a need for improved tissue-specific delivery of contrast agents. Accordingly, it is an object of the invention to provide tissue-specific agents that are capable of binding multiple contrast agents without losing tissue-specificity.

It is a further object of the invention to combine novel tissue-specific contrast agents with nucleic acids to provide delivery vehicles useful in gene delivery and therapy. Such gene delivery can be monitored by way of the presence or absence of the contrast agent.

These and other objects and features of the invention will become apparent to those skilled in the art from the following detailed description and appended claims. The objects are achieved by cell-specific delivery vehicles and methods wherein such delivery vehicles are capable of delivering at least an imaging contrast agent to the targeted cell or tissue. In some embodiments the delivery vehicle is constructed to deliver additional specific molecules (e.g. nucleic acids).

In one embodiment of the invention, an MRI contrast agent delivery vehicle is provided that is capable of enhancing the observed contrast of specific cells and tissues by MRI by targeting cell-surface receptors on such cells or tissue. The delivery vehicle comprises a) a first polymeric molecule having a net positive or negative charge, b) at least one second polymeric molecule having a net charge opposite that of the first polymeric molecule and complexed with the first polymeric molecule, the second polymeric molecule having attached thereto at least one cell targeting moiety, and c) at least one contrast agent attached to the first or second polymeric molecule (see FIGS. 1A and 1B) or to a third polymeric molecule (see FIG. 1C), wherein the third polymeric molecule, if present, has a net charge opposite that of the first polymeric molecule and is complexed with the first polymeric molecule. Thus, the invention can use signal amplification following polycation/polyanion complex formation to induce signal enhancement for MRI.

In another embodiment, one of the polymeric molecules comprises a nucleic acid which is complexed with one or more polymeric molecules comprising a polyamine, so that the resulting contrast agent delivery vehicle is capable of delivering genetic material as well as a contrast agent in a cell or tissue-specific manner.

BRIEF DESCRIPTION OF THE DRAWINGS

FIG. 1A depicts a delivery vehicle (1) wherein a first polymeric molecule (2) having a net positive or a net negative charge is complexed with a second polymeric molecule (3) having a net charge opposite that of the first polymeric molecule. At least one cell targeting moiety (4) and at least one contrast agent (5) are attached to the second polymeric molecule.

FIG. 1B depicts a delivery vehicle (1) wherein a first polymeric molecule (2) having a net positive or a net negative charge is complexed with a second polymeric molecule (2) having a net charge opposite that of the first polymeric molecule. At least one cell targeting moiety (3) is attached to the second polymeric molecule and at least one contrast agent (4) are attached to the first polymeric molecule.

FIG. 1C depicts a delivery vehicle (1) wherein a first polymeric molecule (2) having a net positive or a net negative charge is complexed with a second polymeric molecule (3) having a net charge opposite that of the first polymeric molecule. A third polymeric molecule (6) having a charge opposite that of the first polymeric molecule is complexed with the first polymeric molecule. At least one cell targeting moiety (4) is attached to the first polymeric molecule and at least one MRI contrast agent (5) is attached to the third polymeric molecule.

FIG. 2 compares the level of gene expression of cells transfected with DNA complexed with Gd-DTPA-poly-D-lysine (column 1) to cells transfected with particles which lack the Gd-DTPA-poly-D-Lysine component (column 2). In column 3, free transferrin was added to the solution to competitively inhibit uptake of the gene delivery vehicles (both with and without Gd-DTPA-poly-D-lysine). In all cases 6 μg of DNA was complexed with 3 μg transferrin polylysine (Tf) and 4 μg Gd-DTPA modified poly-D-lysine or unmodified poly-L-lysine (PLL). Error bars represent 1 standard deviation (n–5).

FIG. 3 compares the MRI image obtained from cells transfected with gene delivery vehicles containing Gd-DTPA-poly-D-lysine (1 and 2) to those lacking the GD-DTPA-poly-D-lysine (3 and 4). Note the intense signal indicative of Gd contrast enhancement in 1. In 2 and 4, free transferrin was added to competitively inhibit uptake of the particle. In all cases 12 μg of DNA was complexed with 6 μg transferrin polylysine and 14 μg Gd-DTPA modified poly-D-lysine or unmodified poly-L-lysine.

FIG. 4 depicts the Gd chelating agents, diethylenetriaminepentaacetic acid (DTPA) and 1,4,7,10-tetraazacyclododecane -N,N',N'',N'''-tetracetic acid (DOTA), and p-aminobenzyl-DOTA.

DETAILED DESCRIPTION OF THE INVENTION

Prior to the invention, there were no safe and effective means for targeted delivery of contrast agents to specific cells or tissue using cell-surface receptors. As used herein, the term "contrast agent" includes the various contrast agents that are known for medical imaging. For MRI, the contrast agent can comprise paramagnetic or superparamagnetic metals. These include iron, copper, manganese, chromium, erbium, europium, dysprosium, holmium and gadolinium. Preferred metals are iron, manganese and gadolinium; most preferred is gadolinium. The same features that make the invention advantageous for MRI are relevant to other imaging modalities. Gamma and positron emission tomography are also effective imaging technologies in clinical diagnostic use. Contrast agents that are useful for positron emission tomography may be used in place of paramagnetic chelates to enhance images and include $^{19}$fluorine and $^{11}$carbon or chelates emitting gamma particles such as $^{51}$chromium, $^{68}$gallium, $^{99}$technetium and $^{111}$indium. In addition, contrast agents for optical and fluorescence microscopy can also be used. Especially useful agents for such applications include fluorescein and rhodamine and their derivatives. Agents that induce both optical contrast and photosensitivity include derivatives of the phorphyrins, anthraquinones, anthrapyrazoles, perylenequinones, xanthenes, cyanines, acridines, phenoxazines and phenothiazines [Diwu, Z. J. and Lown, J. W., *Pharmacology and Theraeutics* 63: 1–35 (1994); Grossweiner, L. I., *American Chemical Society Symposium Series* 559: 255–265 (1994)].

The delivery vehicles of the invention and their usage represent a departure from current MRI and optical imaging agents and techniques. As indicated in FIG. 1A, the delivery vehicle (1) comprises a first polymeric molecule (2) having an overall net positive or negative charge which is employed as a scaffold to which an oppositely charged second polymeric molecule (3) is complexed. As shown in FIG. 1B, some delivery vehicles include a third polymeric molecule (6) having a net charge opposite that of the first polymeric molecule and complexed with the first polymeric molecule. Preferably the first and second polymeric molecules are held together by electrostatic interactions and thus do not need to be covalently linked to each other. In certain embodiments, both the first and second polymeric molecules contain a mixture of charged groups and thus are zwitterionic. The depiction of linear polymeric molecules in FIG. 1 is for illustrative purposes and is not necessarily preferred. The delivery vehicle will be in any configuration that is suitable for cellular uptake.

The second polymeric molecule has attached to it at least one cell targeting moiety (4) that renders the delivery vehicles of the invention cell or tissue specific. The selection of cell targeting moiety will depend upon the particular cell or tissue to be targeted. The invention is exemplified below using transferrin as the targeting moiety, to which growing cells have surface receptors. However, any targeting moiety can be utilized in the invention as long as it is capable of being either directly or indirectly attached to the second polymeric molecule and of being specifically bound to and in some cases taken into a targeted cell. For example, the targeting moiety may be an antibody that is directed to a cell surface receptor. Alternatively, protein and glycoprotein ligands, viral receptors and targets, steroid hormones, peptides, carbohydrates, glycolipids as well as ligand analogs, drugs and toxins with cell and tissue specific distributions can be used to target the cells.

In one embodiment of the invention, the contrast agent delivery vehicle does not have a cell-targeting moiety and in general is not cell or tissue specific. In this embodiment, the polymeric molecule having a net positive charge is preferably modified to incorporate hydrophobic residues which facilitate cellular uptake. Cellular uptake of complexes of nucleic acids and polycations having hydrophobic backbones are known in the art [Jean-Paul Behr, *Bioconjugate Chemistry* 5: 382–389 (1994)]. In another embodiment of the invention, the contrast agent delivery vehicle has both a cell-targeting moiety (to generate cell and tissue-specificity) and hydrophobic residues to enhance transfection efficiency.

The second polymeric molecule (3) and/or third polymeric molecule (6), if present, have attached thereto at least one contrast agent.

When the contrast agent delivery vehicle is to be used for MRI, the contrast agent, in a preferred embodiment, is a paramagnetic ion. There is a rapidly growing body of literature demonstrating the clinical effectiveness of various paramagnetic contrast agents. However, a presently preferred paramagnetic contrast agent is chelated gadolinium (Gd), because of its large effect on $T_1$ relaxivity, very high magnetic moment $\mu^2=63BM^2$), and symmetric electronic ground state, ($S^8$). Gd-chelates are also preferred because they are presently the only FDA approved paramagnetic MRI contrast agents.

Gd ions are extremely toxic to cells and therefore must be bound to a chelating agent which is then conjugated to the polymeric molecule.

DTPA chelates and thus acts to detoxify lanthanide ions. The stability constant (K) for $Gd(DTPA)^{2-}$ is very high (logK=22.4) and is more commonly known as the formation constant. The water soluble $Gd(DTPA)^{2-}$ chelate, which is depicted in FIG. 4, is stable, nontoxic, and one of the most widely used contrast enhancement agents in experimental and clinical imaging research. It is an extracellular agent that accumulates in tissue by perfusion dominated processes. Transformation of the DTPA chelating ligand into an intracellular and tissue specific agent generally involves modifying the ligand structure by appending one or more functional groups preferably to the ethylene diamine backbone. The carboxylic acid side chains can also be used as a site for further conjugation. However, this latter approach is not preferred because it can suffer from loss in complex stability due to the replacement of one of the chelating "claws" of DTPA.

By comparison, a macrocyclic framework can be chemically modified without perturbing the binding ability of the ligand and therefore the in vivo stability of the metal chelate complex. The macrocyclic ligand DOTA, shown in FIG. 4, is the preferred structure to base the new class of contrast agents. The synthetic versatility of the macrocyclic skeleton provides an ideal candidate for the synthesis of the target bifunctional agents. As discussed earlier, the key to exploiting the relaxation properties of an MRI contrast agent without lowering the physiological stability is to functionalize (e.g. tissue specific or metabolic probe sites) the molecule while not perturbing the binding site of the metal atom.

In order to fulfill this requirement, the DOTA ligand is modified to accommodate the targeting group or groups. Several literature methods have appeared for the synthetic modification of the DOTA macrocycle [Moi et al. *J. Am. Chem. Soc.* 110:6266 (1988); McMurry et al. *Bioconi. Che.* 3(2):108 (1992); Ren et al. *Bioconj. Che.* 3(6):563 (1992); Kumar et al. *Inorg. Chem.* 32(20):4193 (1993)]. In one method, a p-aminobenzyl moiety is introduced into the DOTA ligand using a tetrapeptide starting material [Moi et al., supra]. The structure of p-aminobenzyl-DOTA is depicted in FIG. 4. The method of preparing the tetrapeptide starting material can be modified using solution methods to add a greater degree of flexibility in the synthesis of the product. The desired ligand can be prepared by variation of literature procedures. The resulting macrocyclic ligand framework fulfills the design features of a successful in vivo contrast agent.

When the first polymeric molecule is polyanionic (i.e. a polymer having a net negative charge), it will preferably comprise a molecule based on heparin, polygalacturonic acid, mucin, nucleic acids and their analogs including those with modified ribose-phosphate backbones, the polypeptides polyglutamate and polyaspartate, as well as carboxylic acid, phosphoric acid, and sulfonic acid derivatives of synthetic polymers. Preferred polyanions are ribonucleic and deoxyribonucleic acids (RNA and DNA). When RNA or DNA is used as the first polymeric molecule, the delivery vehicles of the invention can perform the additional function of delivering genetic material to a cell. Hence, this embodiment encourages a novel clinical protocol in which nucleic acids for gene therapy and agents for MRI contrast are co-transported to specific cells (e.g., cells of a neoplastic tumor) allowing medical imaging monitoring of nucleic acid delivery and therapy in real time.

In some situations, it may be desirable to deliver RNA or single stranded DNA because of its short half-life. For example, one could transfect cells with the contrast agent delivery vehicle and select for transfected cells or show that they were transfected by assaying, for example, for the presence of a reporter gene in the single stranded nucleic acid. In such situations, the transfected cells would not stably integrate the reporter gene. This would be advantageous in situations where wild type cells are desired, such as in tissue grafting and stem cell therapy. In these cases, a utility of the delivery vehicle lies in the ability to readily label the cells with contrast agents, ultimately allowing non-invasive imaging of the grafted cells. Where no DNA integration is desired, other polyanions can be used such as polyaspartate, polyglutamate, heparin and long chain carbohydrates.

The polyanion acts as a negatively charged molecular scaffold to which a positively charged polymer (polycation) is complexed. Thus the polyanion and the polycation will have sufficient charge so that when combined, the two polymeric molecules form a polycomplex under physiological conditions. Generally, after complex formation, the polycomplexes are approximately electrically neutral.

It is known that some nucleic acid vectors can deliver genes up to 100 kilobases in length, and artificial chromosomes (megabases) have been delivered to yeast. Therefore, there is no general size limit to the polyanion. Although, for efficient receptor-mediated uptake, it is preferred that the nucleic acid be less than 100 kilobases, with 5 to 50 kilobases being the most preferred size.

Generally the size of the polycation for nucleic acid complex formation will be less than about 500 monomer residues. Preferred polycations include synthetic polycations based on acrylamide and 2-acrylamido-2-methylpropanetrimethylamine, poly(N-ethyl-4-vinylpyridine) or similar quarternized polypyridine, diethylaminoethyl polymers and dextran conjugates, polymyxin B sulfate, lipopolyamines, poly(allylamines) such as the strong polycation poly(dimethyidiallylammonium chloride), polyethyleneimine, polybrene, spermine, spermidine and polypeptides such as protamine, the histone polypeptides, polylysine, polyarginine and polyornithine. A particularly preferred polycation is polylysine. When poly amino acids such as polylysine and polyarginine are used, preferred sizes are from about 10 to about 200 residues.

Numerous gadolinium (Gd) ions, can be attached to the polyamine or to produce a polycation capable of both enhancing MRI contrast and of complexing to nucleic acid. Modification of up to about 20% of amino group side chains with image-enhancing compounds and/or cell-targeting moieties leaves about 80% or more of the amino groups charged at physiologic pH for interaction with a polyanion. The resulting nucleic acid based MRI contrast agent delivery vehicle contains between 1,000 and 10,000 paramagnetic ions, orders of magnitude more than any previous strategy. Thus, targeted MRI contrast enhancement is achieved at physiologically reasonable concentrations of this agent using standard MRI hardware. Polyamines such as spermine and spermidine are modified at a single nitrogen or carbon leaving a sufficient number of amines for protonation to interact with a polyanion. Histones and protamine are modified at sites not involved in ionic interactions with polyanions such as at cysteine residues in protamine.

Maximal numbers of contrast agents are desired without inhibition of the polycation/polyanion complex formation and without adverse toxic or osmotic effects. In a preferred embodiment of this invention, $Gd^{3+}$ in its chelated form is attached to polylysine at a ratio of from about 2 lysine monomers per Gd chelate to about 100 lysine monomers per Gd chelate. Particularly preferred ratios are from about 4 to about 10 lysine monomers per Gd chelate. Preferred ratios of other cations or anions to Gd chelates are from about 4 monomers to about 20 depending on the strength of the ionic interaction of the polycation/polyanion complexes.

The number of cell-targeting moieties per complex can vary from 0 (such as when hydrophobic polycations are used for nonspecific DNA transformation) to more than 1,000 cell-targeting moieties per complex. A preferred number of cell-targeting moieties per complex is generally from about 10 to about 50 depending on the size of the complex. In one embodiment where transferrin is used as the cell-targeting moiety and poly-L-lysine is the polycation, approximately 1 transferrin to about 100 lysine monomers is a preferred ratio.

When polylysine is used as the second polymeric molecule, the —$NH_2$ groups of the lysine side chains at high pH serve as strong nucleophiles for multiple attachment of activated chelating agents. The invention takes advantage of both the polycationic and polynucleophilic nature of polyamines such as polylysine. At high pH the lysine monomers are coupled to the paramagnetic ion chelators under conditions that yield on average 5–20% monomer substitution. At physiologic pH to low pH, the remaining unlabeled positively charged lysines facilitate nucleic acid binding. Both optical isomers of polylysine can be used. The D isomer has the advantage of having long-term resistance to cellular proteases. The L isomer has the advantage of being more rapidly cleared from the subject.

Polylysine can also serve as the polymeric molecule to which a cell targeting moiety is attached. Polylysine coupled to ligands for cell-surface receptors such as transferrin [Wagner et al., Proc. Natl. Acad. Sci. USA 87:3410–3414 (1991)] and asialoglycoprotein [Wu et al., J. Biol. Chem. 2:14338–14342 (1991)] facilitate the receptor mediated uptake of DNA. The —$NH^{3+}$ groups of the lysine side chains at neutral pH are used to complex with the negatively charged phosphate backbone of the DNA. Electrically neutral complexes of the polyanionic DNA and the polycationic polylysine-protein conjugates form what is thought to be toroidal particles capable of delivering DNA into specific cells at relatively high efficiency [Wagner et al., Proc. Natl. Acad. Sci. USA 88:4255–4259 (1991)]. Improvements to this technique include complex formation with hydrophobic polycations to increase transfection efficiency and cotransfection with adenovirus particles [Wagner et al., Proc. Natl. Acad. Sci. USA 89:6099–6103 (1992)] or conjugation of fusogenic peptides to the polylysine [Wagner et al., Proc. Natl. Acad. Sci. USA 89:7934–7938 (1992)] or transfection in the presence of chloroquine [Wagner et al., Proc. Natl. Acad. Sci. USA 87:3410–3414 (1991)], all to reduce endosomal degradation of the DNA. It has been noticed that modifications to these particles which promote escape from lysosomal degradation pathways can increase gene expression (Wagner et al. PNAS 89:7934–7938 (1992)].

Surprisingly, when a polycomplex of DNA/poly-D-lysine/Gd-DTPA/transferrin is used to transfect cells, a higher efficiency of gene transfection is achieved than when a DNA/poly-D-lysine/transferrin complex is used that lacks an MRI contrast agent. This higher efficiency of GD-DTPA-polylysine is noticed at numerous different ratios of components (see for example FIG. 2) using both D and L isomers of the polylysine. This effect may be due to the increased uptake of Gd-DTPA containing particles or the increased efficiency of their gene expression once inside the cells.

While the nucleic acid-delivery aspects of the invention are demonstrated in the examples below using a DNA sequence that encodes a reporter gene for the enzyme luciferase, other useful sequences can be delivered in a similar manner. Alternatively, instead of using a sequence that encodes proteins, antisense DNA sequences may be used that encode antisense RNA sequences. Clinical uses of the invention may also involve nucleic acids for gene therapy such as genes for lymphokines, growth hormones, exogenous antigens, viral enzymes (susceptibility genes), and genetic regulators, etc. Numerous reference are available that disclose the clinical potentials of gene therapy [e.g. Gutierrez et al. "Gene-Therapy for Cancer" Lancet 339:715–721 (1992); Zatloukal et al. "Somatic Gene-Therapy for Cancer—The Utility of Transferrinfection in Generating Tumor Vaccines: Gene 135:199–207 (1993)]. In addition, DNA or RNA sequences encoding reporter genes and selectable markers can be delivered as well, providing a means to select transfected cells in vitro prior to tissue or cell transplantation. [Demagalhaessilverman et al. "Bone-Marrow Transplantation—A Review" Cell Transplantation 2:75–98 (1993)].

The preparation of the delivery vehicles described herein relies on the synthesis of the three components using modifications of literature techniques, followed by the self-assembly of the complex in solution. A typical reaction scheme is described in the examples below for the preparation of MRI contrast agent/gene delivery vehicles which display the receptor target molecule, transferrin, and contain numerous covalently bound Gd complexes. These examples are set forth so that the invention described herein may be more fully understood. The examples are for illustrative purposes only and are not to be construed as limiting the scope of the invention in any manner.

EXAMPLE 1

Preparation of Transferrin-Poly-L-Lysine

Human apo-transferrin was purified by size exclusion chromatography and dissolved in 30 mM sodium acetate buffer (pH 5.0). At 4° C., 20 molar equivalents of sodium periodate were added. The reaction to oxidize the transferrin carbohydrate (N-acetyineuraminic acid) to its aldehyde form, was allowed to proceed at 4° C. for 120 minutes. The modified transferrin was purified by size-exclusion chromatography and added immediately to a solution containing 0.5 equivalents poly-L-lysine (average chain length=180 subunits) in 100 mM sodium acetate buffer (pH 5.0). The reaction product was reduced to the secondary amine with the addition 800 equivalents of sodium cyanoborohydride in four aliquots at 1 hour intervals [Wagner et al., *Proc. Natl. Acad. Sci. USA* 89:7934–7938 (1992)].

The transferrin modified poly-L-lysine was fractionated by size-exclusion chromatography. The fraction determined to contain polylysine modified with on average 2 transferrin molecules per polycation chain was used in subsequent experiments.

EXAMPLE 2

Preparation of DTPA-Poly-D-Lysine

The conjugation of polylysine with DTPA dianhydride was accomplished using modifications of standard literature procedures [Hnatowich et al., *J. Immunol. Methods* 65:147–157 (1983)]. Polylysine modified at 5 to 20% of the monomer sidechains was prepared in order to balance the desire for high signal strength of the Gd-containing particles against the need to maintain the DNA binding capacity of the polycationic chain.

Fifty milligrams of poly-D-lysine (average chain length=180 subunits) was dissolved in 20 ml of 0.5 M sodium carbonate buffer (pH 9.8), and placed in a 50 ml round bottom flask equipped with a stirring bar. Freshly prepared DTPA anhydride was added (100, 200 and 400 fold equivalent excess in separate reactions) in 10 equal portions over a period of 1 hour. The pH of the reaction was maintained at 9.8 by the addition of 3% sodium hydroxide solution. The DTPA modified poly-D-lysine was purified by size exclusion chromatography employing a Pharmacia FPLC system.

In order to evaluate the number of DTPA molecules per lysine chain, aliquots of the purified product were allowed to react with $EuCl_3$ in water. Fluorescence emission measurements of the products (612 nm) were performed on a SLM 8000C spectrofluorimeter versus a series of standards. The total amount of substituted derivatives ranged from 9–11 DTPA/polylysine for the 100 fold excess reaction product to 35 DTPA/polylysine for the 400 fold reaction. The Eu-DTPA-polylysine each reaction were tested for their ability to bind DNA using a UV hyperchromicity assay in which DNA complexed with polycations shows higher absorbance of UV light than uncomplexed DNA. Using this assay, it was found that the least heavily modified polylysine (10 $Eu^{3+}$'s per polylysine) bound DNA as well as unmodified polylysine; the most heavily modified polylysine did not bind DNA at all; and the moderately labeled polylysine showed reduced DNA binding affinity.

The compound with an average 10 DTPA sites per polylysine was allowed to chelate with a 1.1 molar excess of $Gd(Cl)_3$ in distilled water at pH 7.0 for 3 hours at 70° C. The Gd-DTPA-poly-D-lysine was purified by gel filtration and used in subsequent experiments.

EXAMPLE 3

Formation of Tissue-Specific/MRI Contrast Agent Complex

The "GeneLight" plasmid was purchased from Promega Corp. (Madison, Wis.) and prepared in large quantities using standard procedures. This plasmid contains the luciferase gene (*P. pyralis*) under the control of the SV40 enhancer/promoter resulting in strong luciferase expression in mammalian cells, such as the K562 human line used in this study. The expression of this gene is easily monitored by measuring light production in extracts of transfected cells.

Typically, 6 µg of plasmid was added to suboptimal quantities of transferrin-polylysine in 0.5 ml HEPES buffered saline (150 mM sodium chloride, 20 mM HEPES, pH 7.3) and allowed to form complexes for 10 minutes at room temperature [Wagner et al., *Proc. Natl. Acad. Sci. USA* 88:4255–4259 (1991)]. Varying amounts of poly-D-lysine or Gd-DTPA-poly-D-lysine were added to the solution to completely neutralize the negative charge by forming ternary complexes with the DNA.

EXAMPLE 4

DNA Expression in Targeted Cells

K562 cells were grown in suspension in RPMI medium plus 10% fetal calf serum, 100 units/ml penicillin, 100 µg/ml streptomycin and 2 mM glutamine. The Gd-DTPA-polylysine/DNA/transferrin-polylysine complexes formed were added to 2 ml of a cell suspension containing 500,000 cells and 100 µM chloroquine, and allowed to incubate at 37° C. for 10 hours. As a control, some cells were simultaneously treated with free transferrin to competitively inhibit the receptor mediated uptake of the MRI contrast agent delivery vehicle. Subsequently the cells were washed into fresh medium and harvested after 18 hours. Cells were washed three times with HEPES buffered saline and lysed in 30 µl of extract buffer.

Immediately after addition of the luciferase substrate and adenosine triphosphate, light emission was assayed with a Beckman scintillation counter. FIG. 2 compares graphically the levels of gene expression observed using gene delivery vehicles which contain Gd-DTPA poly-D-lysine (column 1) with gene delivery vehicles that contain unmodified poly-L-lysine instead of the contrast agent. The addition of the Gd chelate to the polylysine actually enhances the efficiency of gene transfection, an observation noted at other particle compositions as well. With the addition of 20 µg of free transferrin to these experiments, light production indicating efficiency of gene transfection is dramatically reduced (column 3). This effect indicates that the mechanism of gene transfection is indeed transferrin mediated uptake.

EXAMPLE 5

MRI Image Acquisition

MRI images were acquired using a 11.7 Tesla Bruker AMX 500 MHz MRI spectrometer with microimaging accessory. Suspensions of cells identical to those used to assay transfection efficiency were used to obtain the images shown in FIG. 3. Approximately 500,000 cells were transferred to 2 mm glass capillary tubes and allowed to settle out of suspension. The tubes were sealed, and images were acquired using a multi-slice spin echo protocol (TR/TE= 300/13 ms). These parameters result in a $T_1$ lighted image, as is appropriate for Gd based contrast agents.

In FIG. 3. the cells transfected with particles containing Gd-DTPA-poly-D-lysine are shown in 1 and 2. The addition of free transferrin in 2 competitively inhibits uptake of the particles and reduces the MRI contrast. This further confirms that MRI contrast enhancement of these particles is specific and via the transferrin uptake pathway. Thus, the cells treated with particles composed of DNA, transferrin, Gd-DTPA and polylysine show simultaneously efficient gene transfection as well as dramatic MRI contrast enhancement.

All documents referred to herein are hereby expressly incorporated by reference.

What is claimed is:

1. A delivery vehicle comprising:
   a) a nucleic acid vector,
   b) at least a first polylysine molecule substantially complexed with said nucleic acid vector, said first polylysine molecule having attached thereto at least one cell targeting moiety, and
   c) a medical imaging contrast agent comprising DTPA chelated with Gd wherein said DTPA is attached to said first polylysine molecule or to a second polylysine molecule, wherein said second polylysine molecule, if present, is substantially complexed with said nucleic acid vector.

2. A method of delivering a nucleic acid to a cell comprising:
   (a) contacting said cell with a nucleic acid delivery vehicle comprising:
      i) a nucleic acid vector,
      ii) at least a first polylysine molecule substantially complexed with said nucleic acid vector, said first polylysine molecule having attached thereto at least one cell targeting moiety for a surface receptor on said cell, and
      iii) a medical imaging contrast agent comprising DTPA chelated with Gd wherein said DTPA is attached to said first polylysine molecule or to a second polylysine molecule, wherein said second polylysine molecule, if present, is substantially complexed with said nucleic acid vector, and
   (b) detecting the presence of said contrast agent in said cell or an indication of whether said nucleic acid vector has been delivered to said cell.

* * * * *